(12) United States Patent
Hsieh et al.

(10) Patent No.: US 11,752,233 B2
(45) Date of Patent: Sep. 12, 2023

(54) METHOD FOR STERILIZING AMBIENT AIR USING PLASMA-BASED SMART WINDOW

(71) Applicant: Ming Chi University of Technology, New Taipei (TW)

(72) Inventors: Jang-Hsing Hsieh, New Taipei (TW); Nima Bolouki, New Taipei (TW); Shu-Chien Chang, New Taipei (TW); Shi-Wei Huang, New Taipei (TW)

(73) Assignee: Ming Chi University of Technology, New Taipei (TW)

( * ) Notice: Subject to any disclaimer, the term of this patent is extended or adjusted under 35 U.S.C. 154(b) by 635 days.

(21) Appl. No.: 17/002,961

(22) Filed: Aug. 26, 2020

(65) Prior Publication Data

US 2021/0060201 A1 Mar. 4, 2021

(30) Foreign Application Priority Data

Aug. 28, 2019 (TW) ................. 108130848

(51) Int. Cl.
| | | |
|---|---|---|
| *A61L 9/22* | (2006.01) | |
| *E06B 7/28* | (2006.01) | |
| *H05H 1/24* | (2006.01) | |
| *H01J 19/08* | (2006.01) | |
| *A61L 2/14* | (2006.01) | |
| *H05H 1/46* | (2006.01) | |

(52) U.S. Cl.
CPC ............... *A61L 9/22* (2013.01); *A61L 2/14* (2013.01); *E06B 7/28* (2013.01); *H01J 19/08* (2013.01); *H05H 1/2406* (2013.01); *A61L 2209/11* (2013.01); *H05H 1/2431* (2021.05); *H05H 1/466* (2021.05)

(58) Field of Classification Search
CPC ................. A61L 2/14; A61L 9/22; E06B 7/28
See application file for complete search history.

(56) References Cited

U.S. PATENT DOCUMENTS

| | | | |
|---|---|---|---|
| 2019/0235342 A1* | 8/2019 | Wang | ........................ E06B 9/24 |
| 2021/0022234 A1* | 1/2021 | Polak | ........................ A61L 2/26 |
| 2021/0068242 A1 | 3/2021 | Hsieh et al. | |

FOREIGN PATENT DOCUMENTS

| | | |
|---|---|---|
| TW | 201132368 A1 | 10/2011 |
| TW | I694748 B | 5/2020 |

OTHER PUBLICATIONS

Search Report issued in TW109128037 dated Jan. 21, 2021.

* cited by examiner

*Primary Examiner* — Timothy C Cleveland
(74) *Attorney, Agent, or Firm* — THE WEBB LAW FIRM

(57) ABSTRACT

A method for sterilizing ambient air includes the steps of: a) installing a plasma-based smart window including an atmospheric pressure plasma device which includes first and second transparent flat patterned electrodes sandwiched between a light-transmissive substrate and a light-transmissive cover plate; and b) applying a power supply parameter of a predetermined magnitude between the first and second transparent flat patterned electrodes at ambient temperature and pressure to generate a surface plasma proximate to the light-transmissive substrate or the light-transmissive cover plate so as to inactivate microorganisms in the ambient air.

5 Claims, 5 Drawing Sheets

$1 \times 10^4$ CFU/ml
Before treatment

147 CFU/ml
After treatment $1 \times 10^3$ CFU/ml
Before treatment

4 CFU/ml
After treatment

METHOD FOR STERILIZING AMBIENT AIR USING PLASMA-BASED SMART WINDOW

CROSS-REFERENCE TO RELATED APPLICATION

This application claims priority to Taiwanese Patent Application No. 108130848 filed Aug. 28, 2019, the disclosure of which is hereby incorporated by reference in its entirety.

BACKGROUND OF THE INVENTION

Field of the Invention

The disclosure relates to a method for sterilizing ambient air, and more particularly to a method for sterilizing ambient air using a plasma-based smart window.

DESCRIPTION OF RELATED ART

According to a survey conducted by the Centers for Disease Control and Prevention, an estimated 1.7 million hospital-associated infections in the United States are caused by microorganisms, such as bacteria, fungi, etc.

There are several conventional methods for disinfection and sterilization, which include pressurized hot air (at a temperature of 170° C.), pressurized hot water vapor (at a temperature of 120° C.), use of toxic substances, and the like. However, such methods have some limitations in use. For instance, use of toxic substances might adversely affect a surface on which the toxic substances are applied. In addition, the aforementioned methods cannot be suitably used inside a room or spaces in a building.

The preparation of a medium having a large area, which is capable to sterilize an interior space, would be useful.

SUMMARY OF THE INVENTION

Therefore, an object of the disclosure is to provide a method for sterilizing ambient air, especially in an interior space, which does not involve use of toxic substances, which may be implemented at an ambient temperature, and which are environmentally friendly.

According to the disclosure, there is provided a method for sterilizing ambient air. The method includes the steps of:
a) installing a plasma-based smart window including
a frame, and
an atmospheric pressure plasma device installed on the frame and including
a light-transmissive substrate,
a first transparent flat patterned electrode disposed on the light-transmissive substrate,
a second transparent flat patterned electrode disposed on the light-transmissive substrate and spaced apart from the first transparent flat patterned electrode by a predetermined gap distance, and
a light-transmissive cover plate covering the first and second transparent flat patterned electrodes so as to permit the first and second transparent flat patterned electrodes to be sandwiched between the light-transmissive substrate and the light-transmissive cover plate; and
b) applying a power supply parameter of a predetermined magnitude between the first and second transparent flat patterned electrodes at ambient temperature and pressure to generate a surface plasma proximate to the light-transmissive substrate or the light-transmissive cover plate so as to inactivate microorganisms in the ambient air.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
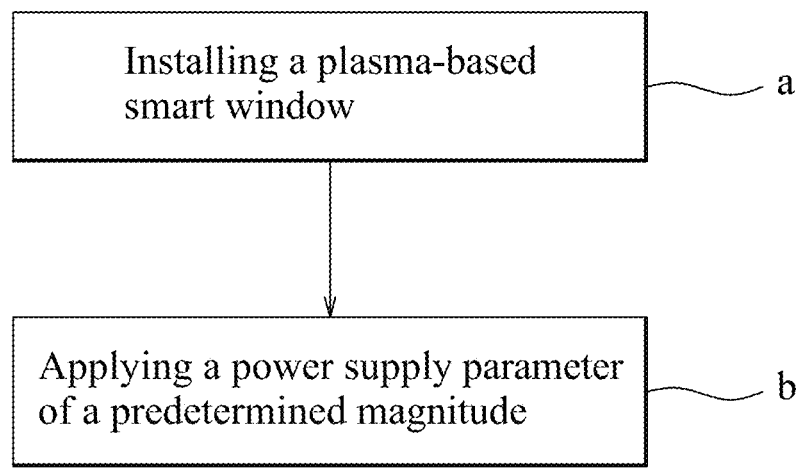
FIG. 1 is a flow diagram of an embodiment of a method for sterilizing ambient air according to the disclosure.
Figure 2:
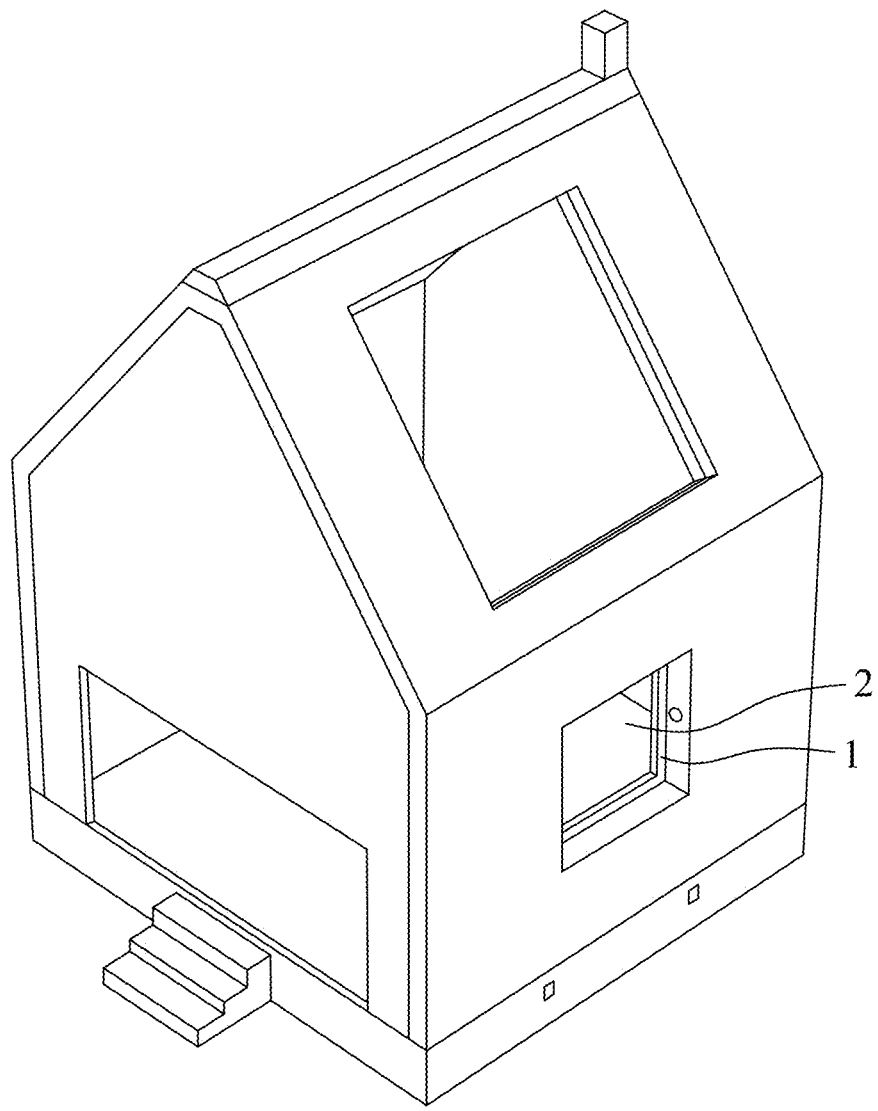
FIG. 2 is a schematic perspective view of a model building installed with a plasma-based smart window for implementation of the embodiment of the method for sterilizing ambient air according to the disclosure.
Figure 3:
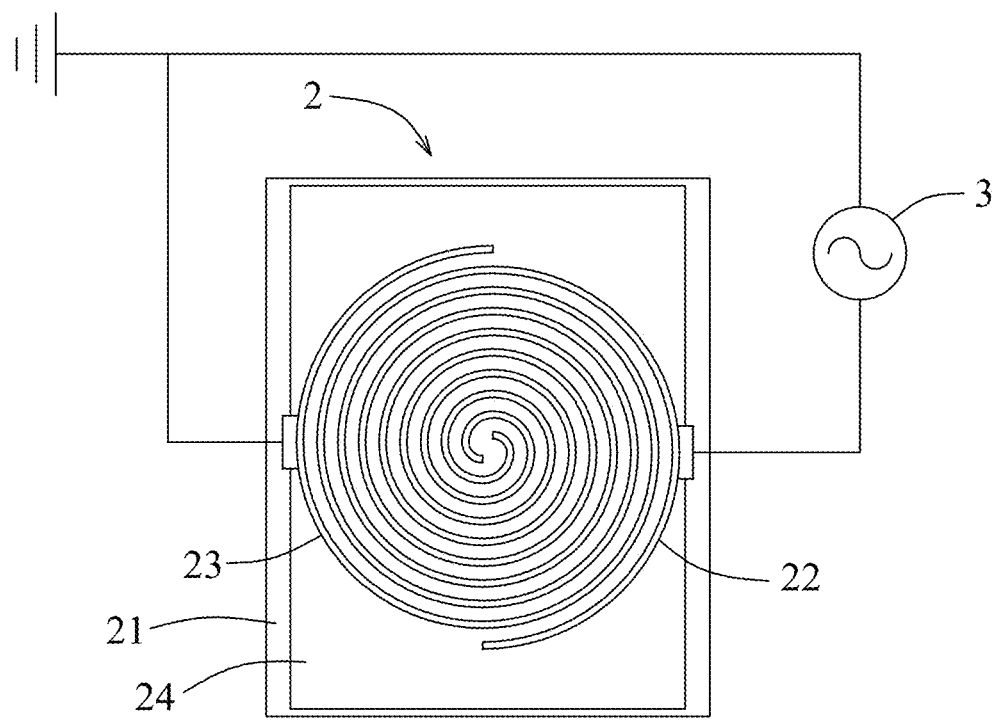
FIG. 3 is a schematic view showing a configuration of an atmospheric pressure plasma device included in the plasma-based smart window.

Referring to FIGS. 1 to 3, an embodiment of a method for sterilizing ambient air includes the steps of a) installing a plasma-based smart window, and b) applying a power supply parameter of a predetermined magnitude.

In step a), the plasma-based smart window includes a frame 1 and an atmospheric pressure plasma device 2 installed on the frame 1.

The atmospheric pressure plasma device 2 includes a light-transmissive substrate 21, a first transparent flat patterned electrode 22, a second transparent flat patterned electrode 23, and a light-transmissive cover plate 24.

The first transparent flat patterned electrode 22 is disposed on the light-transmissive substrate 21. The second transparent flat patterned electrode 23 is disposed on the light-transmissive substrate 21, and is spaced apart from the first transparent flat patterned electrode 22 by a predetermined gap distance. The predetermined gap distance may range, for example, from 0.8 mm to 1.2 mm. The light-transmissive cover plate 24 covers the first and second transparent flat patterned electrodes 22, 23 so as to permit the first and second transparent flat patterned electrodes 22, 23 to be sandwiched between the light-transmissive substrate 21 and the light-transmissive cover plate 24.

Figure 4:
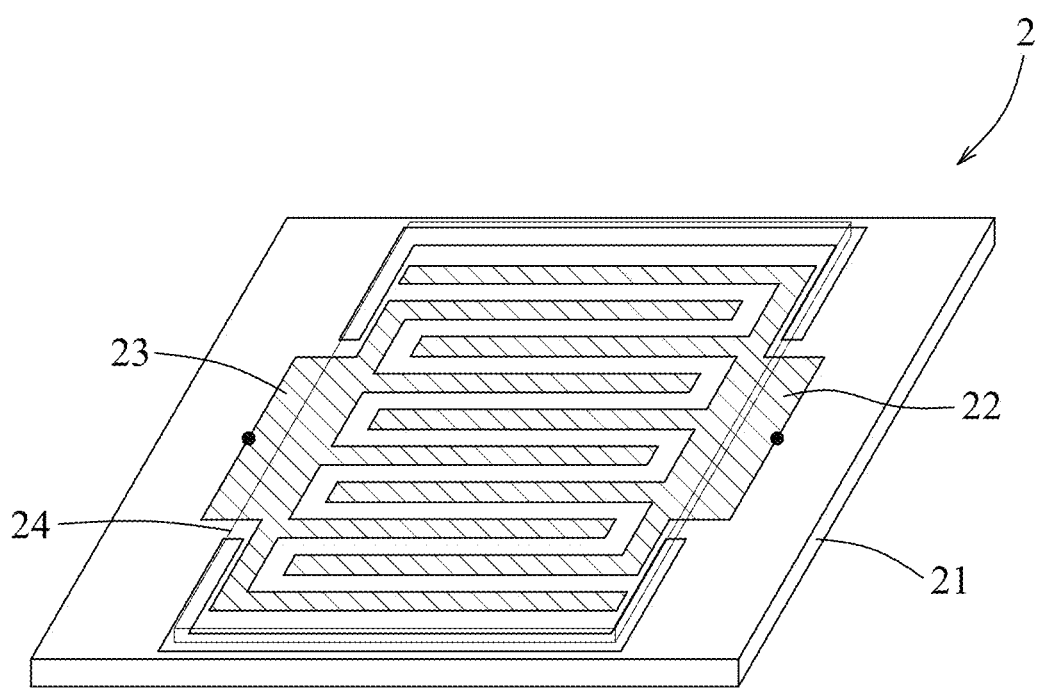
FIG. 4 is a schematic top view of another configuration of the atmospheric pressure plasma device included in the plasma-based smart window.

The light-transmissive substrate 21 and the light-transmissive cover plate 24 may be made of, for example, a quartz glass. The first and second transparent flat patterned electrodes 22, 23 may be made of, for example, indium tin oxide (ITO), indium zinc oxide (IZO), or indium gallium zinc oxide (IGZO), and may be configured as transparent flat spiral electrodes as illustrated in FIG. 3 or transparent flat interdigitated electrodes as illustrated in FIG. 4. Further details regarding the atmospheric pressure plasma device 2 can be obtained by referring to U.S. patent application Ser. No. 16/827,215, which corresponds to Taiwanese Invention Patent Application No. 108130848 and has been published as U.S. patent application No. 2021/0068242, which is entirely incorporated herein by reference.

In step b), a power supply parameter of a predetermined magnitude is applied between the first and second transparent flat patterned electrodes 22, 23 at ambient temperature and pressure to generate a surface plasma proximate to the light-transmissive substrate 21 or the light-transmissive cover plate 24 so as to inactivate microorganisms in the ambient air. The power supply parameter may be a power supply voltage, power supply current, or a a power supply frequency. When the power supply parameter is a power supply voltage, the predetermined magnitude ranges from 7.5 kV to 8.5 kV, and the voltage waveform may be a sinusoidal form or a pulsed form. When the power supply parameter is a power supply current, the predetermined magnitude may be in the order of several tens milliamperes (mA), for example, up to 70 mA. When the power supply parameter is a power supply frequency, the predetermined magnitude may be in the order of several tens of kilohertz (kHz), for example, ranging from 10 kHz to 20 kHz. The power supply parameter is applied from a power supply 3. Further details regarding the power supply 3 can be obtained by referring to U.S. patent application Ser. No. 16/823,215.

The method for sterilizing ambient air according to the disclosure can be used in a building that has a facade made from glass to offer a window-related air disinfection. Specifically, the method according to the disclosure can be used in medical institutions and hospitals, where pathogen infections are widespread, to sterilize the ambient air.

The plasma generated by the method according to the disclosure permits the air in the atmospheric pressure to ionize so as produce active species and radicals, such as hydroxyl radicals, oxygen radicals, and ozone, which can inactivate the microorganisms in the ambient air, so as to sterilize the interior of the building.

The method for sterilizing ambient air according to the disclosure can offer several advantages, such as free of toxic chemical materials, low-operating temperature, and environmental friendliness.

Specifically, a non-thermal atmospheric pressure plasmas generated by the method according to the disclosure can provide energetic electrons, active species, and ultraviolet radiation, without significant increase in atmospheric temperature. The energetic electrons are responsible to generate short-lived species, such as oxygen radicals and hydroxyl radicals, and long-lived species, such as ozone. Such species enable the plasma to be highly reactive chemically. The energetic electrons are also capable of breaking hydrogen bonds of organic molecules which form the microorganisms. In addition, the active species can be dissolved inside water to form a biofilm that can destroy cell walls of the microorganisms so as to inactivate the microorganisms.

Examples of the disclosure will be described hereinafter. It is to be understood that these examples are exemplary and explanatory and should not be construed as a limitation to the disclosure.

Example 1

$E.\ coli$ in a concentration of $1.0 \times 10^4$ CFU/ml was applied on an agar plate, which was then placed within the model building as shown in FIG. 2, followed by supplying an AC power of 8 kV and 16 kHz from a high voltage power supply (Model: PG103301-AC1; Manufacturer: You-Shang Technical Corp., Taiwan) to a plasma-based smart window installed in the model building and then detecting an ozone concentration within the model building using an ozone detector (Model: EST-1015H-03-200 PPM; Manufacturer: Environmental Sensor Technology Co. Inc.), so as to control the ozone concentration within the model building at a range from 8 ppm to 15 ppm. The treatment procedure was conducted for 5 minutes after plasma was generated.

The concentration of $E.\ coli$ remained on the agar plate after the treatment procedure was determined by the naked eye, and was estimated to be 147 CFU/ml.

The result is shown in FIG. 4 and is summarized in Table 1.

Example 2

The treatment procedure of Example 2 is similar to that of Example 1 except that $E.\ coli$ in a concentration of $1.0 \times 10^3$ CFU/ml was used for the treatment procedure in Example 2.

Figure 5:
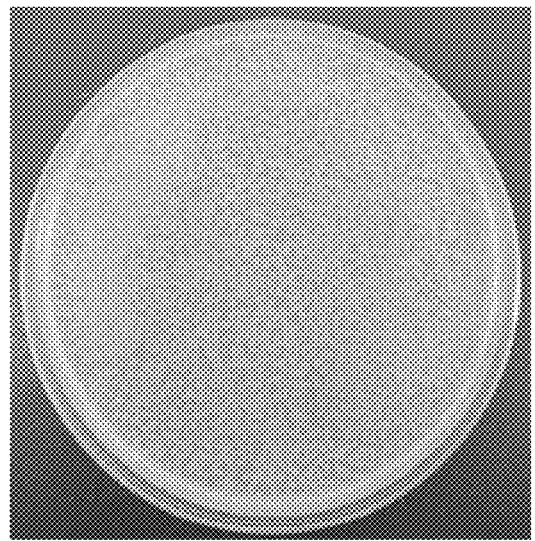
FIG. 5 shows photographs comparing results of a first test specimen before and after treatment with an embodiment of a method for sterilizing ambient air according to the disclosure.
Figure 5:
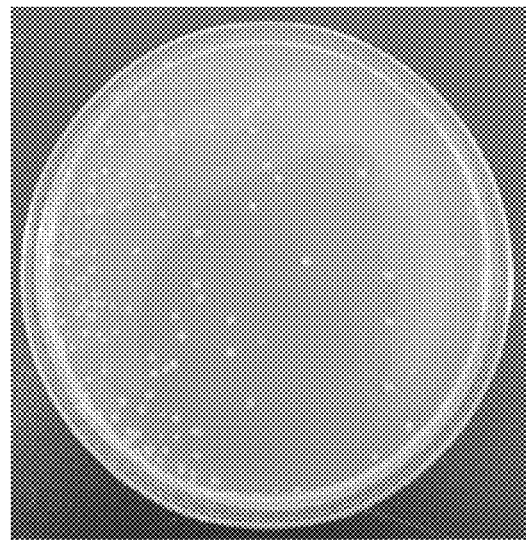
Figure 6:
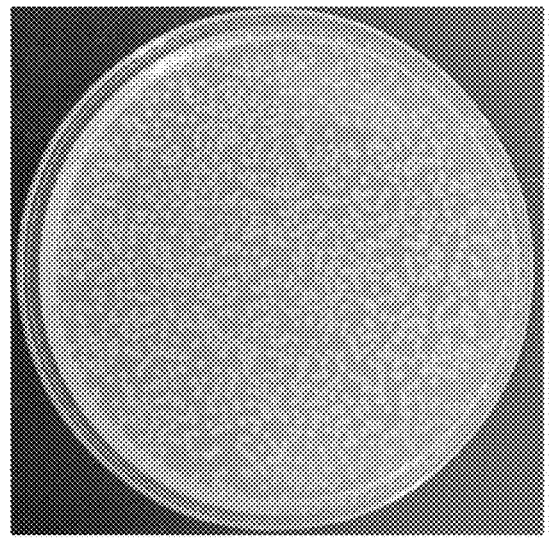
FIG. 6 shows photographs comparing results of a second test specimen before and after treatment with the embodiment of the method for sterilizing ambient air according to the disclosure.
Figure 6:
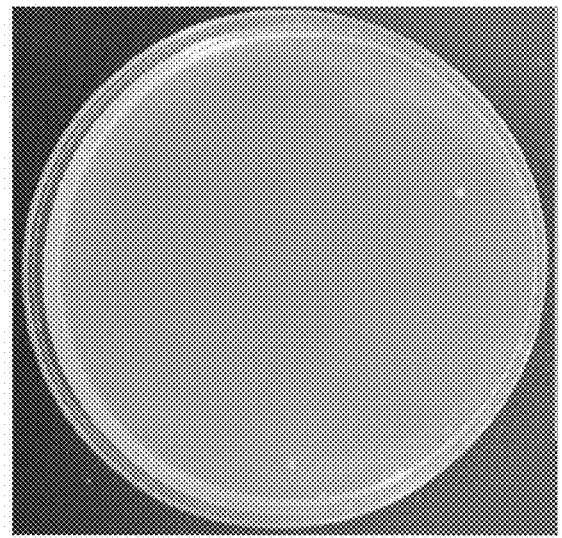

The result is shown in FIG. 5 and is summarized in Table 1.

TABLE 1

| | Concentration of $E.\ coli$ before treatment | Concentration of $E.\ coli$ after treatment |
|---|---|---|
| Example 1 | $1.0 \times 10^4$ CFU/ml | 147 CFU/ml |
| Example 2 | $1.0 \times 10^3$ CFU/ml | 4 CFU/ml |

As shown in Table 1, in Examples 1 and 2, by virtue of the method for sterilizing ambient air using the plasma-based smart window according to the disclosure, the concentration of $E.\ coli$ significantly decreases after the treatment procedure compared with that before the treatment procedure.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:
1. A method for sterilizing ambient air, comprising the steps of:
 a) installing a plasma-based smart window comprising:
  a frame, and
  an atmospheric pressure plasma device installed on the frame, the atmospheric pressure plasma device comprising:

a light-transmissive substrate, a first transparent flat patterned electrode disposed on the light-transmissive substrate, a second transparent flat patterned electrode disposed on the light-transmissive substrate and spaced apart from the first transparent flat patterned electrode by a predetermined gap distance, and a light-transmissive cover plate covering the first and second transparent flat patterned electrodes so as to permit the first and second transparent flat patterned electrodes to be sandwiched between the light-transmissive substrate and the light-transmissive cover plate; and b) applying a power supply parameter of a predetermined magnitude between the first and second transparent flat patterned electrodes at ambient temperature and pressure to generate a surface plasma proximate to the light-transmissive substrate or the light-transmissive cover plate so as to inactivate microorganisms in the ambient air.

2. The method according to claim 1, wherein in step b), the power supply parameter is a power supply voltage, and the predetermined magnitude ranges from 7.5 kV to 8.5 kV.

3. The method according to claim 1, wherein in step b), the power supply parameter is a power supply current, and the predetermined magnitude is up to 70 mA.

4. The method according to claim 1, wherein in step b), the power supply parameter is a power supply frequency, and the predetermined magnitude ranges from 10 kHz to 20 kHz.

5. The method according to claim 1, wherein in step a), the predetermined gap distance ranges from 0.8 mm to 1.2 mm.

* * * * *